United States Patent [19]
Nash et al.

[11] Patent Number: 5,411,520
[45] Date of Patent: May 2, 1995

[54] HEMOSTATIC VESSEL PUNCTURE CLOSURE SYSTEM UTILIZING A PLUG LOCATED WITHIN THE PUNCTURE TRACT SPACED FROM THE VESSEL, AND METHOD OF USE

[75] Inventors: John Nash, Downingtown; Douglas Evans, Devon, both of Pa.

[73] Assignee: Kensey Nash Corporation, Exton, Pa.

[21] Appl. No.: 12,816

[22] Filed: Feb. 3, 1993

Related U.S. Application Data

[63] Continuation-in-part of Ser. No. 846,322, Mar. 15, 1992, Pat. No. 5,282,827, which is a continuation-in-part of Ser. No. 789,704, Nov. 8, 1991, Pat. No. 5,222,974.

[51] Int. Cl.⁶ .............................................. A61B 17/00
[52] U.S. Cl. ..................................... 606/213; 606/151; 128/887; 604/900
[58] Field of Search .................. 606/1, 213, 215, 151; 128/887; 600/32; 604/51, 168, 900; 623/11

[56] References Cited

U.S. PATENT DOCUMENTS

| | | | |
|---|---|---|---|
| 3,871,379 | 3/1975 | Clarke | 606/148 |
| 3,874,388 | 4/1975 | King et al. | 606/213 |
| 4,007,743 | 2/1977 | Blake | 606/213 |
| 4,317,445 | 3/1982 | Robinson | 604/168 |
| 4,890,612 | 1/1990 | Kensey | 623/1 |
| 5,035,701 | 7/1991 | Kabbara | 606/144 |
| 5,053,046 | 10/1991 | Janese | 606/213 |
| 5,108,420 | 4/1992 | Marks | 606/213 |
| 5,108,421 | 4/1992 | Fowler | 606/213 |
| 5,171,259 | 12/1992 | Inoue | 606/213 |
| 5,192,301 | 3/1993 | Kamiya et al. | 606/213 |
| 5,254,133 | 10/1993 | Seid | 606/213 |

FOREIGN PATENT DOCUMENTS

WO90/14796 12/1990 WIPO .................. 606/213

*Primary Examiner*—Stephen C. Pellegrino
*Assistant Examiner*—Jeffrey A. Schmidt
*Attorney, Agent, or Firm*—Caesar, Rivise, Bernstein, Cohen & Pokotilow, Ltd.

[57] ABSTRACT

A system, a closure, and method for sealing a percutaneous puncture in a blood vessel. The puncture includes a tract leading to it from the skin of the being. The system includes an introducer sheath, a positioning device, a hemostatic puncture closure, and a deployment instrument. The positioning device positions the introducer sheath at a desired position within the vessel. The deployment instrument includes a tubular carrier having a distal end storing the closure. The carrier is extended via an introducer sheath through the tract and puncture into the blood vessel. The closure comprises a rigid anchor, a spacer member, a compressed collagen plug, and a thin filament connecting them in a pulley-like arrangement. The anchor has a centrally located domed projection. The carrier ejects the anchor through the introducer and puncture and then draws it against the free end of the introducer. The instrument and introducer are then withdrawn together to pull the anchor against the tissue contiguous with the puncture inside the artery and so that the domed portion of the anchor extends through the puncture. Further withdrawal draws the plug and spacer out of the carrier into the puncture tract, whereupon the spacer engages the domed portion of the anchor to prevent the plug from entering the puncture. A tensioning device limits the force applied to the filament. The carrier also includes a tamper which is used to mechanically deform the plug within the tract. Hemostasis occurs rapidly and the plug seals the tract.

60 Claims, 8 Drawing Sheets

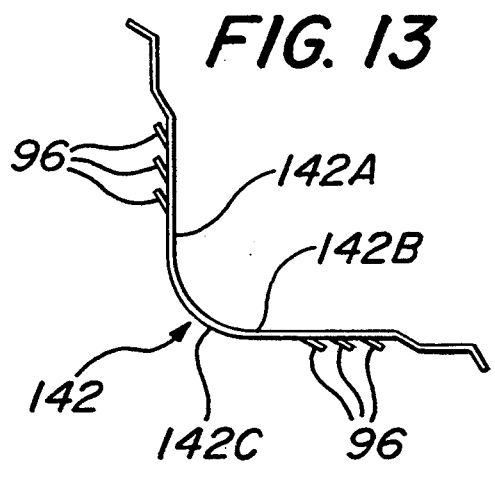
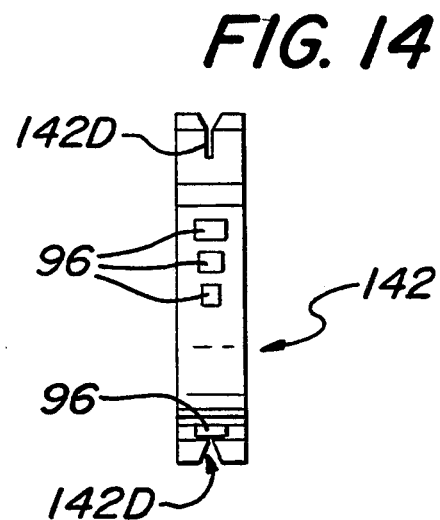
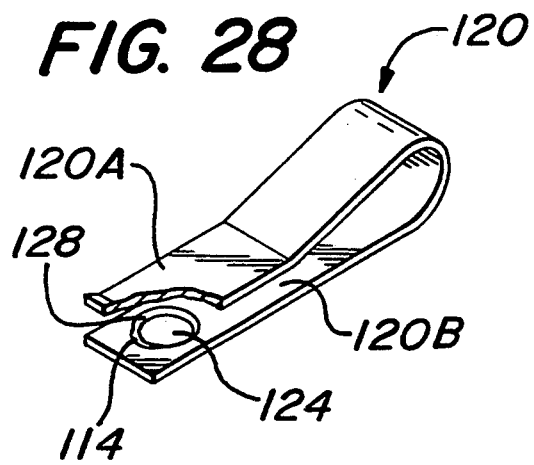
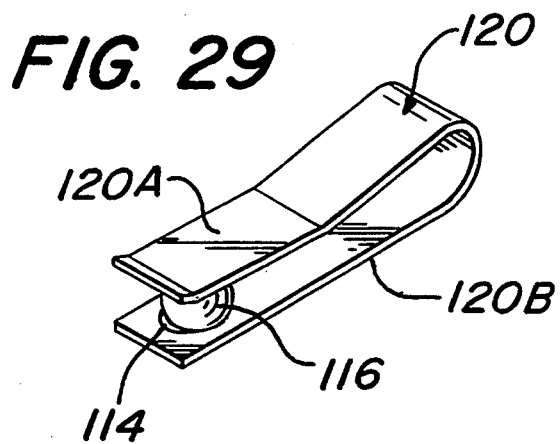
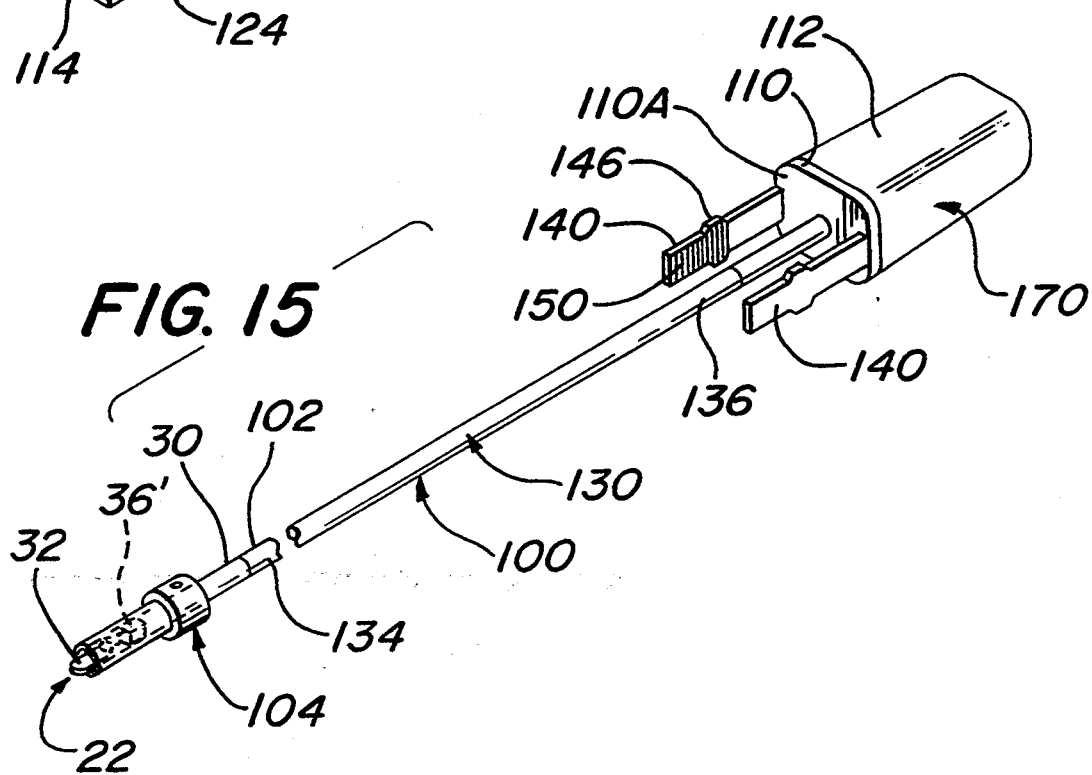

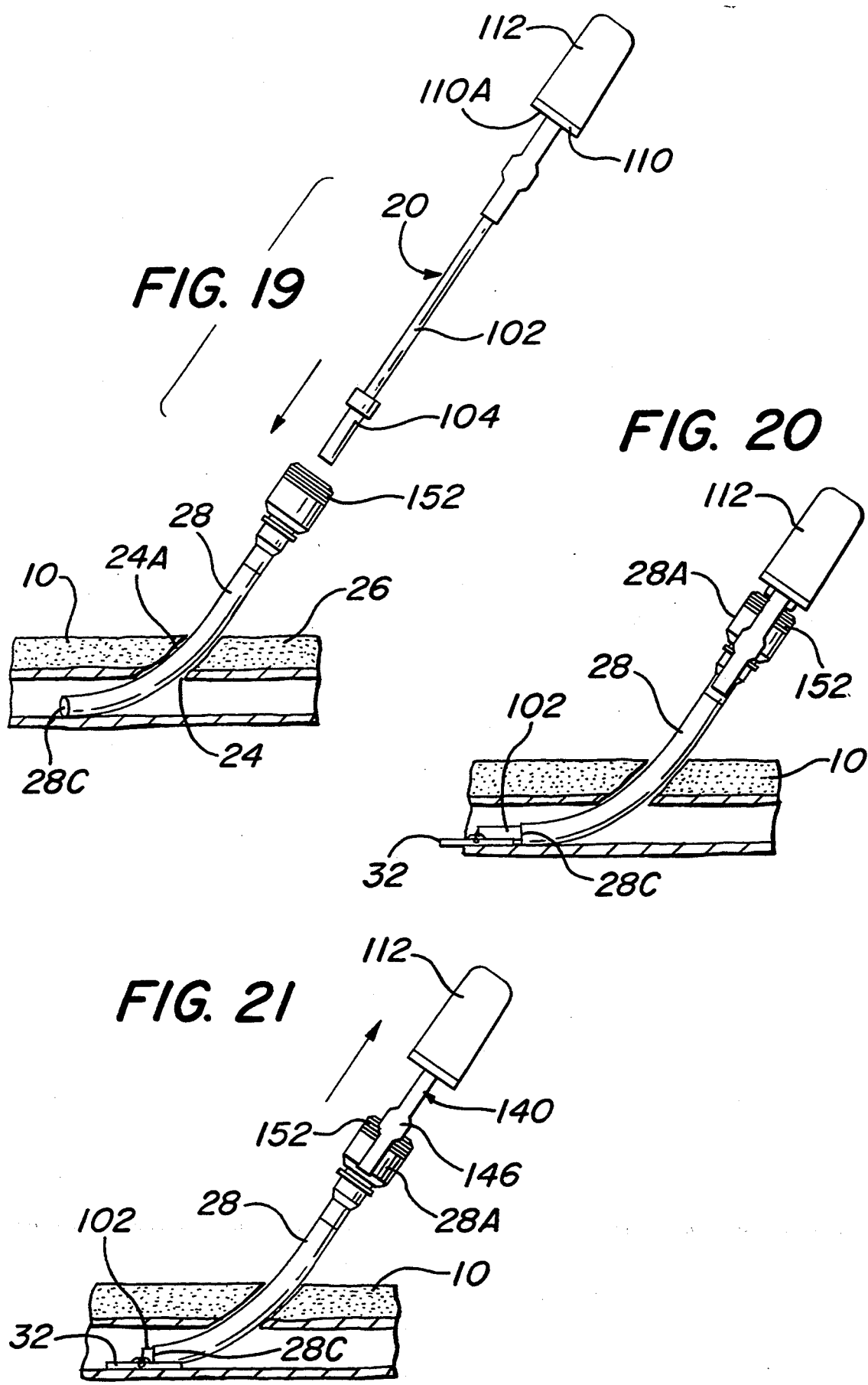

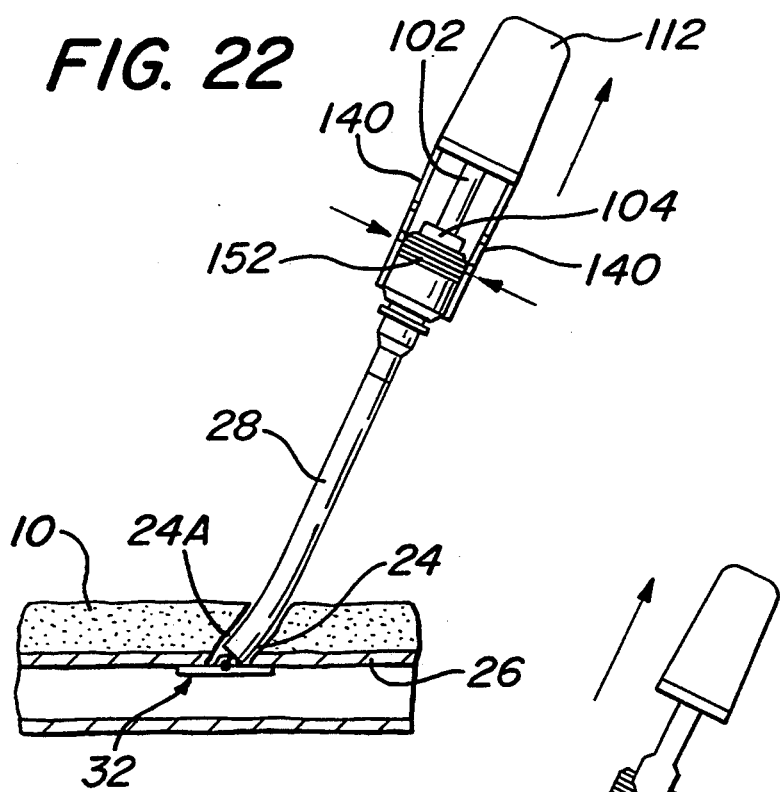
FIG. 22
FIG. 23
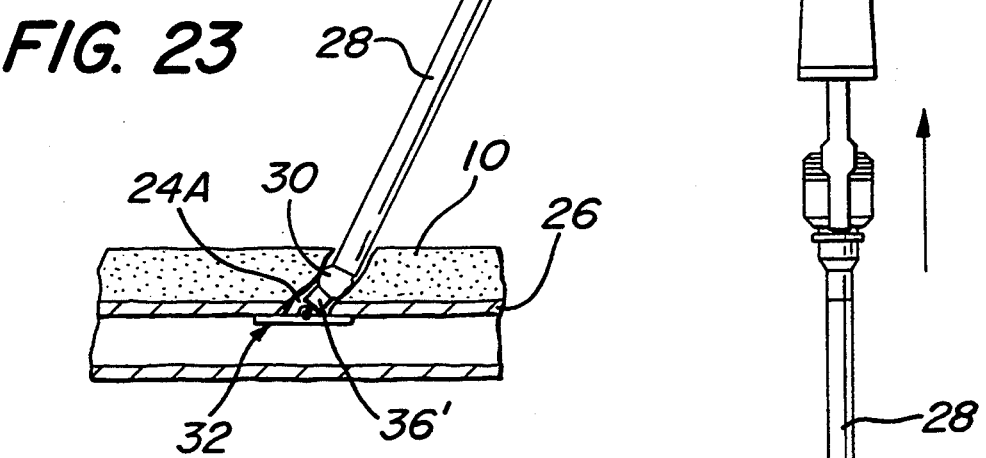
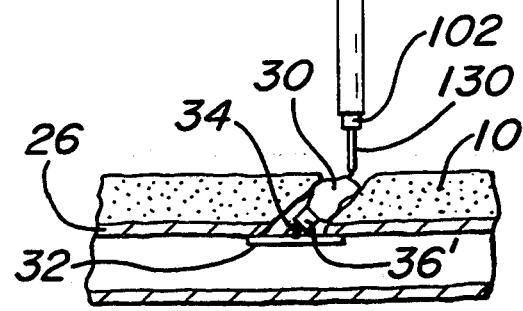
FIG. 24

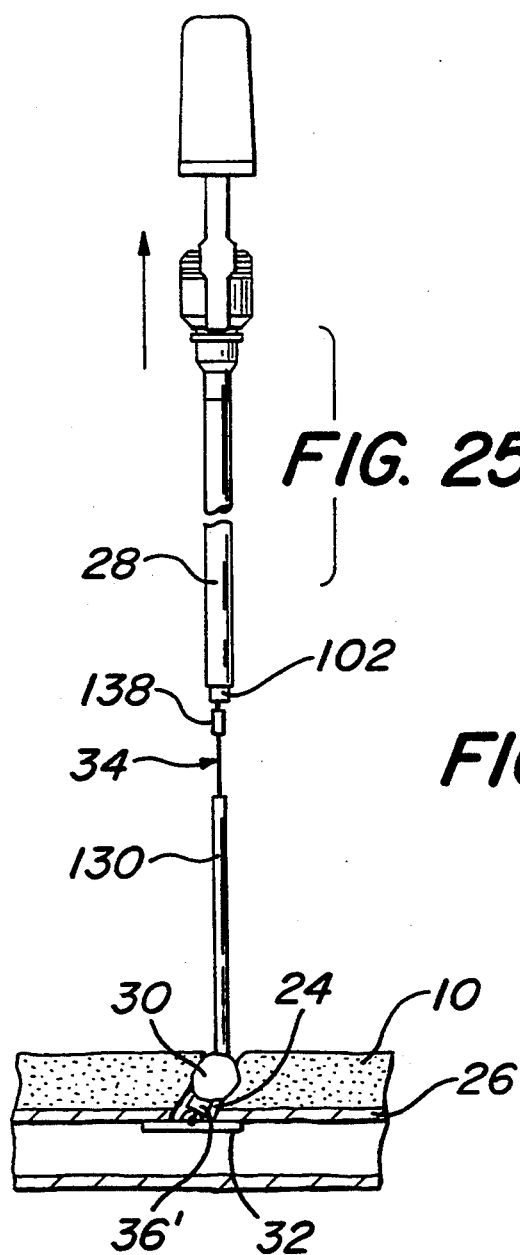
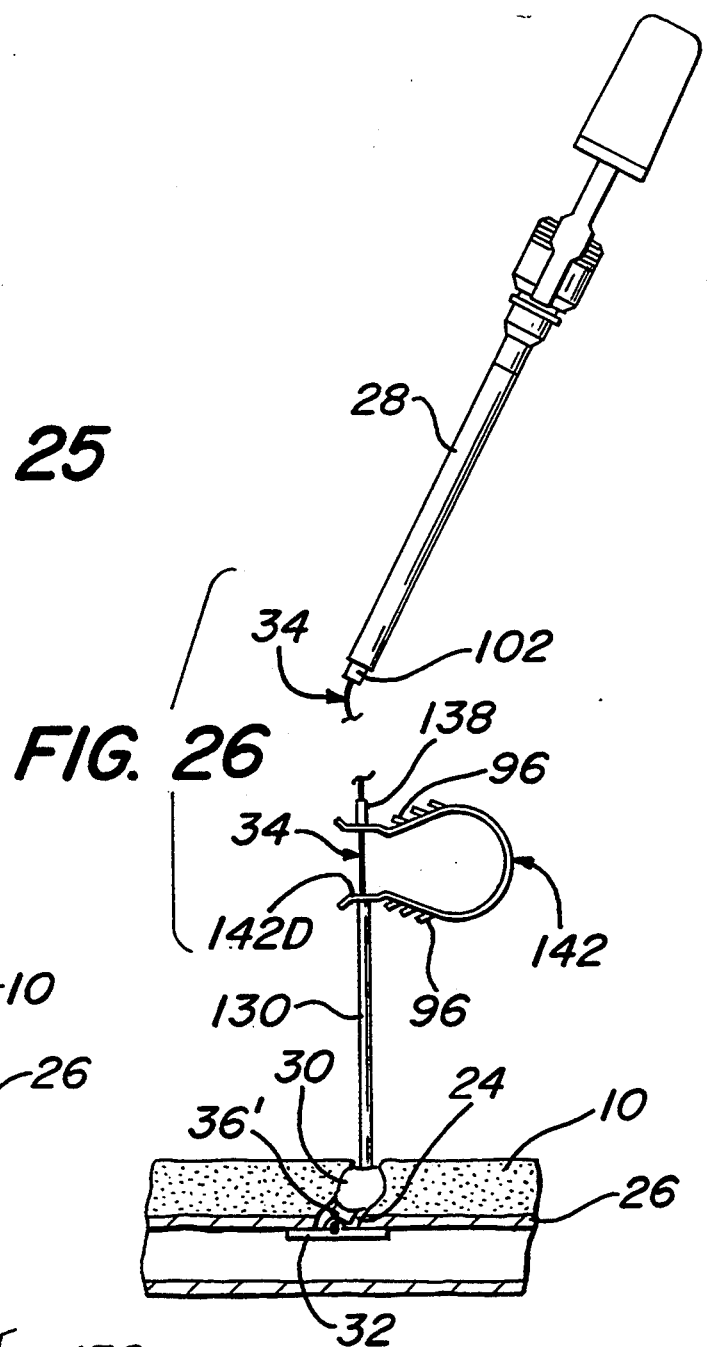
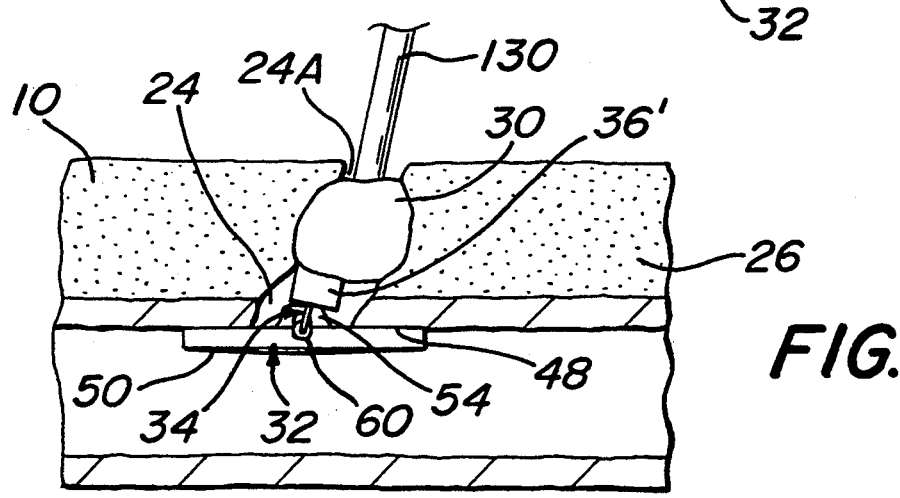
FIG. 25
FIG. 26
FIG. 27

HEMOSTATIC VESSEL PUNCTURE CLOSURE SYSTEM UTILIZING A PLUG LOCATED WITHIN THE PUNCTURE TRACT SPACED FROM THE VESSEL, AND METHOD OF USE

This application is a Continuation-In-Part of U.S. patent application Ser. No. 07/846,322, filed on Mar. 5, 1992, entitled Hemostatic Puncture Closure System and Method of Use, now U.S. Pat. No. 5,282,827, which is itself is a Continuation-In-Part of U.S. patent application Ser. No. 07/789,704 filed on Nov. 8, 1991, entitled Hemostatic Puncture Closure System and Method of Use, now U.S. Pat. No. 5,222,974, both of which applications are assigned to the same assignee as this invention, and whose disclosures are incorporated by reference herein.

BACKGROUND OF THE INVENTION

In U.S. Pat. No. 5,021,059, which has also been assigned to the same assignee as this invention, there is disclosed a closure device and method of use for sealing a small incision or puncture in tissue separating one portion of the body of a living being from another portion thereof, e.g., a percutaneous puncture in an artery, to prevent the flow of a body fluid, e.g., blood, through the puncture. The closure device is arranged to be used with (deployed by) an instrument which comprises a carrier in the form of a tubular member. The tubular member has a proximally located portion and a distally located portion. The latter includes an open free end arranged to be introduced through the incision or puncture. The proximately located portion of the tubular member is arranged to be located out of the body of the being when the distally located portion is extended through the incision or puncture. The closure device comprises three components, namely, an anchor member, a sealing member, and a filament, e.g., suture. The anchor member includes a tissue engaging portion configured to pass through the puncture in one direction but resistant to passage therethrough in the opposite direction. The sealing member is formed of a hemostatic material, such as compressed collagen foam, and has a tissue engaging portion. The filament is connected between the anchor member and the sealing member in a pulley-like arrangement so that they may be moved relative to each other by the application of a pulling force on the filament. The instrument is arranged to expel the anchor member through the puncture, e.g., into the artery, and to draw its tissue engaging portion into engagement with the tissue contiguous with the puncture. The filament extends through the instrument to a point outside the body of the being and is arranged to be drawn in the proximal direction, whereupon the portion of the filament connecting the anchor member causes the tissue engaging portion of the sealing member to move with respect to the anchor member, thereby drawing the anchor member and sealing member together. This action causes the tissue engagement portion of the sealing member to seal the puncture from the flow of fluid therethrough. The closure device and deploying instrument in that patent have left something to be desired from the standpoints of effectiveness and efficiency of use. The inventions of the two foregoing applications of which this application is a Continuation-In-Part, were designed to improve upon the invention of U.S. Pat. No. 5,021,059.

In particular, in copending U.S. patent application Ser. No. 07/846,322, filed on Mar. 5, 1992, entitled Hemostatic Puncture Closure System and Method of Use, there is disclosed an claimed an improved system for sealing a percutaneous puncture in a blood vessel of a living being, with the puncture comprising a opening in the wall of the blood vessel and a tract contiguous with that opening and extending through tissue overlying the blood vessel. That system basically comprises carrier means, introducer means, and closure means. The closure means comprises anchoring means, sealing means, and filament means, with the filament means coupling the anchoring means and the sealing means. The introducer means comprises a tubular member having a distal free end insertable into the puncture tract and through the opening in the blood vessel wall.

The carrier means is insertable through the introducer means and includes means to expel the anchoring means therefrom. Moreover, the carrier means is retractable with respect to the introducer means after the anchoring means has been expelled from the carrier means, so that when it is retracted it draws the anchoring means into engagement with the distal free end of the introducer means.

The introducer means and the carrier means are coupled for movement together to draw the anchoring means which is now in engagement with the distal end of the introducer means into engagement with the interior tissue of the vessel generally adjacent the opening in the wall thereof.

The filament means is operative to move the anchoring means and the sealing means relative to each other to cause the sealing means to engage tissue generally adjacent the puncture outside of the vessel.

While the closure and deployment system of the aforementioned patent applications are suitable for their intended purposes, they still may leave something to be desired from one or more of the following standpoints: simplicity of construction; ease of deployment and operation; and safety.

OBJECTS OF THE INVENTION

Accordingly, it is a general object of this invention to provide a device and methods of use which overcomes the disadvantages of the prior art.

It is a further object of this invention to provide a system including a closure, a deploying instrument, and method of use for quickly, easily, safely and effectively sealing a percutaneous puncture in a blood vessel within the body of a living being from another portion of the body.

It is still a further object of this invention to provide a closure utilizing sealing means in the puncture tract but spaced from the opening in the wall of the blood vessel to ensure that if any portion of the sealing means should break off it will not enter into the blood vessel.

It is yet a further object of this invention to provide a closure deploying instrument which is simple in construction.

SUMMARY OF THE INVENTION

These and other objects of this invention are achieved by providing a system for sealing a percutaneous incision or puncture in a blood vessel. The system comprises carrier means, introducer means, and closure means. The puncture comprises a tract extending through tissue overlying the blood vessel. In the preferred embodiment, the closure device comprises four components, namely, an anchor member, a sealing member, a spacer member, and a filament, e.g., suture. The anchor member includes a tissue engaging portion configured to pass through the puncture in one direction but resistant to passage therethrough in the opposite direction. The sealing member is formed of a hemostatic material, such as compressed collagen foam. The spacer member is mounted upon the suture, and is slidable thereon, and is positioned between the anchor member and the sealing member. The filament member is connected between the anchor member and the sealing member in a pulley-like arrangement so that the members may be moved relative to each other by the application of a pulling force on the filament. The instrument is arranged to expel the anchor member through the puncture, e.g., into the artery, and to draw its tissue engaging portion into engagement with the tissue contiguous with the puncture.

The filament extends through the instrument to a point outside the body of the being and is arranged to be drawn in the proximal direction, whereupon the portion of the filament connecting the anchor member and the sealing member causes the sealing member to move with respect to said anchor member and into engagement with the spacer member thereby drawing the anchor member, spacer member and sealing member together. This action causes the sealing member to seal the puncture from the flow of fluid therethrough.

The presence of the spacer member prohibits the sealing member from contacting the arterial wall and thereby possibly entering into the artery where a portion could conceivably break off and flow distally or cause the creation of an embolism.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 13 is a side elevation view of a torsion spring used with the deployment instrument of this invention;

FIG. 14 is a front elevation view of the spring shown in FIG. 13;

FIG. 15 is an isometric view of the deployment instrument shown in FIG. 1 having the closure located at its distal end;

FIGS. 19-26 are illustrations, similar to FIGS. 16 and 17, but showing the sequential steps in the use of the instrument to deploy the closure device to seal the percutaneous puncture in the artery;

FIG. 27 is an enlarged illustration showing the closure device in place after it has sealed the percutaneous puncture in the artery;

FIG. 28 is an enlarged illustration showing the spring used in the tensioning mechanism of the instrument;

FIG. 29 is an enlarged illustration similar showing the spring and ball used in the tensioning mechanism of the instrument.

DETAILED DESCRIPTION OF THE PREFERRED EMBODIMENT

Figure 1:
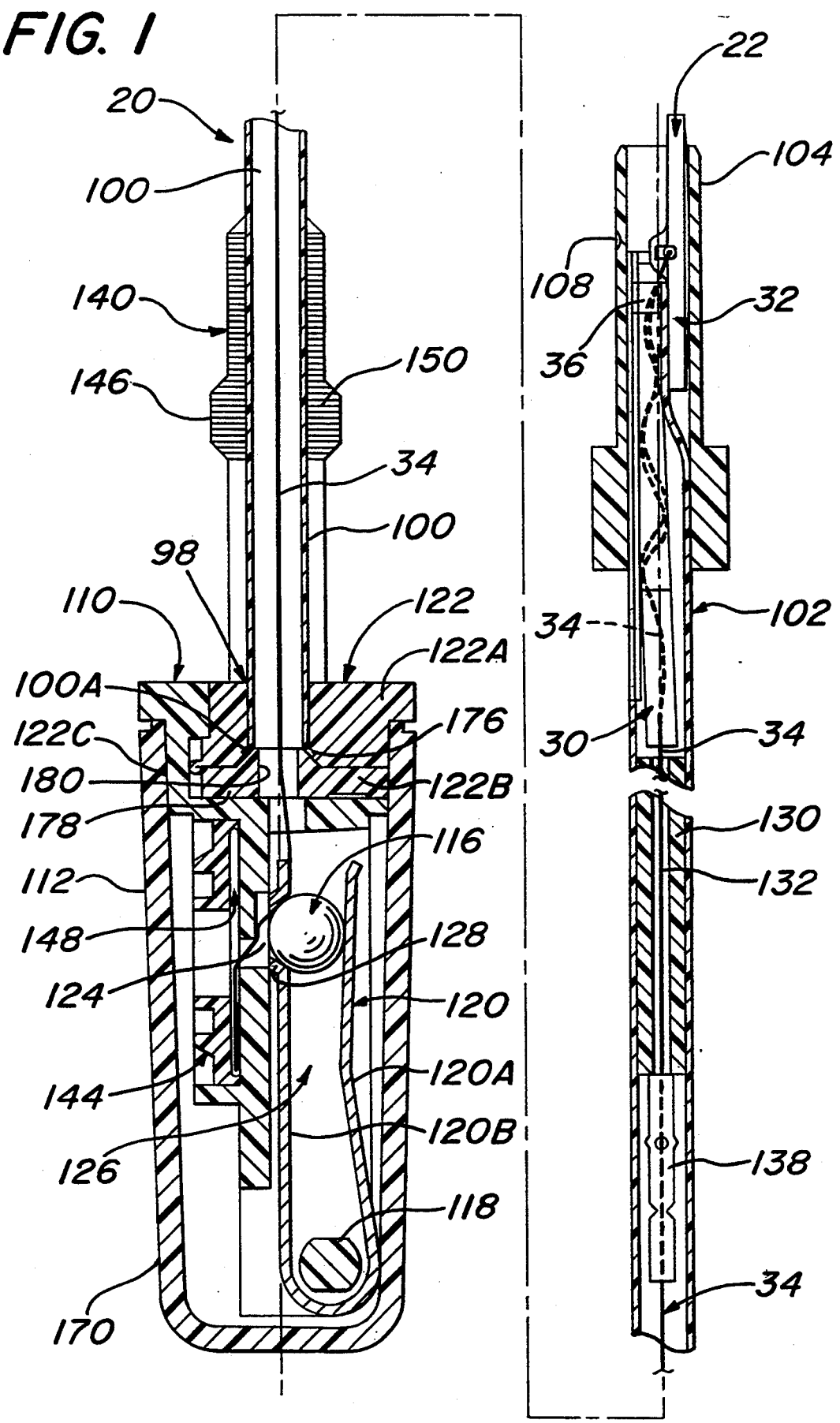
FIG. 1 is a side elevation view, partially in section, showing a deploying instrument and a closure device of the system of the subject invention.

Referring now in greater detail to the various figures of the drawings wherein like reference characters refer to like parts, there is shown at 20 an instrument forming a portion of a system for deploying a closure device 22 to seal a percutaneous puncture 24 within a blood vessel 26, e.g., the femoral artery, constructed in accordance with this invention. As shown clearly in FIGS. 16 and 17, the puncture 24 includes not only the opening in the wall of the vessel but also the tract 24A, i.e., the passageway in the tissue 10 located between the vessel and the skin of the being formed when the vessel is punctured. The instrument 20 and closure device 22 have particular utility when used in connection with intravascular procedures, such as angiographic dye injection, cardiac catheterizations, balloon angioplasty and other types of recanalizing of atherosclerotic arteries, etc., since the closure 22 is designed to cause immediate hemostasis of the blood vessel, e.g., arterial, puncture. However, it is to be understood that while the description of the preferred embodiment instrument and closure contained herein is directed to the closing off of percutaneous incisions or punctures in arteries, they have much more wide-spread applications. Thus, the sealing of a percutaneous opening in an artery shown herein is merely exemplary.

Before describing the closure 22 and the instrument 20 for inserting it to seal the opening, a brief description of a typical, conventional, intravascular surgical procedure, e.g., catheter instrumentation of an artery, utilizing a percutaneous opening will be given to best appreciate the features of the invention. In such a procedure a cannula of an instrument, such as an angiographic needle (not shown), is inserted percutaneously through the skin into the artery, such as the femoral artery, at the situs for the instrument's insertion. The needle cannula is held in place and the flexible end of a guidewire 202 (FIG. 16) is then passed through the cannula into the artery to the desired depth (i.e., a longitudinal position therealong). Once the guidewire is in place the needle cannula is removed, leaving the guidewire in place. An introducer sheath 28 (FIGS. 16 and 17) and an arterial dilator (not shown) are then passed over the guidewire, through the puncture or incision and into the artery. The guidewire and then the dilator are removed leaving the introducer sheath in place. A catheter, or other intravascular instrument (not shown) is then inserted through the introducer sheath 28 and threaded down the artery 26 to the desired intravascular location, e.g., the situs of the atherosclerotic occlusion.

Once the intravascular procedure (e.g., angioplasty) has been completed, the catheter is removed. Thereafter, the sheath is removed and the physician or other trained person applies manual or digital pressure to the percutaneous puncture until hemostasis has occurred. In particular, the current standard of care for puncture hemostasis is to apply digital or mechanical pressure on the puncture site for twenty minutes to an hour, depending on the puncture size and the degree of hemolytic therapy. Obviously this results in wasted time for the physicians and other catheter lab personnel, and causes inconvenience and discomfort for the patient. In addition serious complications arise from persistent bleeding and hematoma formation in approximately five percent of the patients.

In accordance with the method of this invention the introducer sheath 28 is left in place within the artery (although it is moved so that its distal end is at a desired position therein, as will be described later). The deployment instrument 20 having the closure device 22 therein is inserted into the introducer sheath. The closure device is then deployed (ejected) and operated to immediately seal the arterial puncture site 24 and plug the tract 24A.

Moreover, as will be appreciated from the description to follow the closure device 22 is designed to reduce post-procedure puncture complications, cause minimal inflammatory reaction and resorb completely within a relatively short period of time, e.g., sixty to ninety days.

The details of the closure 22 and instrument 20 for introducing it will be described in detail later. Suffice it for now to briefly describe the closure and its method of deployment and use. Thus, as will be seen later the closure has four basic components, namely, a sealing member 30, an intraarterial anchor member 32, a spacer member 36, and a positioning member 34. The sealing member is in the form of an elongated rod-like plug, e.g., a hemostatic resorbable material such as a collagen sponge or foam. This member is arranged for sealing the puncture tract 24A. The anchor member 32 is an elongated, stiff, low-profile, resorbable member which is arranged to be seated inside the artery against the artery wall contiguous with the puncture 24 in the artery's wall. The anchor member 32 is made of non-hemostatic resorbable material e.g., a resorbable polymer similar to a resorbable suture. The position member comprises a flexible filament, e.g., a resorbable suture.

Figure 8:
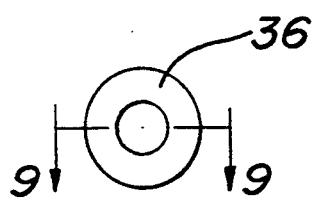
FIG. 8 is an enlarged, top plan view of one preferred embodiment of a spacer component; used in the closure of this invention.
Figure 9:
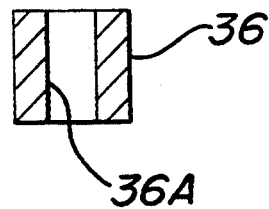
FIG. 9 is a sectional view taken along line 9—9 of FIG. 8.

The spacer member 36 of FIGS. 8 and 9 comprises a cylindrical member with a single longitudinally oriented lumen 36A extending the length thereof. The lumen 36A is arranged to receive therethrough the suture 34 so that it is slidable thereon. The spacer member 36' is similar in construction to 36 except that it includes a pair of longitudinally extending lumens 36'A and 36'B through which the suture 34 extends. Both spacer members 36 and 36' are made of a resorbable material, e.g., a resorbable polymer or gelatin. One or more additives such as a radiopaque material or hemostatic agent or antibacterial agent can be blended into or coated upon the spacer member.

As mentioned earlier, the positioning member 34 comprises a filament, e.g., a resorbable suture. The suture connects the anchor member 32 and the sealing member 30 (collagen plug) via a pulley-like arrangement with the spacer member 36 or 36' located therebetween. Accordingly, when the positioning member is pulled in the proximal direction (as will be described later), this action serves to move the anchor member and plug member together to cause the anchor member to engage the interior surface of the artery contiguous with the puncture, with the spacer member engaging a portion of the anchor member through the puncture, but not engaging the exterior of the artery wall, and with the sealing member engaging the proximal (top) end of the spacer member so that the sealing member is within the puncture tract but remote from the opening in the artery wall.

The closure device 22 is used after the interventional procedure is finished. In particular, the physician inserts the delivery or deployment instrument 20 containing the closure device 22 into the patient's introducer sheath 28. On insertion, the anchor member 32 passes out of the distal end of the introducer sheath 28C so that it is deployed within the artery lumen. The deployment instrument 20 is then withdrawn from the introducer sheath until resistance is felt when the anchor member catches on the distal end thereof. Once this occurs (and assuming that the anchor is in the correct orientation when it catches on the end of the introducer sheath, as will be described later) the deployment instrument 20 and the introducer sheath 28 are then immediately withdrawn together. This withdrawing action causes the anchor member 32 to engage (catch) on the artery wall 26 contiguous with the puncture in the wall. Continued withdrawal of the instrument and introducer sheath causes the pulley-like configuration of the filament 34 to pull the collagen plug 30 and spacer member 36 toward the anchor member 32, thereby depositing the plug in the puncture tract 24A at the exterior of the artery contiguous with the puncture. Neither the spacer member nor the sealing member engage the arterial wall. In this regard the spacer member contacts a dome portion 54 (to be described later) of the anchor member 32 which extends from the interior of the artery through the opening in the artery wall (See FIG. 27). Thus, the spacer member 36 serves to prohibit the sealing member 30 from being pulled into the arterial puncture. The pulling on the filament 34, to bring the spacer and plug into engagement with the anchor dome 54, also has the effect of deforming the plug into a larger diameter body to aid in holding it in place within the puncture tract 24A as shown in FIGS. 24–27 and which will be described later. Moreover, since the plug 30 is formed of compressed collagen or other hydrophilic material it also expands automatically in the presence of blood within the puncture tract 24A when deployed, thereby further contributing to the plug's enlargement.

The instrument 20 also includes a tamper 130 (to be described later) which is mounted on the suture 34 and which is slidable thereon. The deployment of the plug member 20 also effects the deployment of the tamper 130 into the puncture tract 24A proximally of the plug member. The tamper is then used to gently compress and lock the collagen plug on the suture filament within the puncture tract but outside of the artery. The closure 22 is now locked in place through the clotting of the hemostatic collagen plug and by spring tension provided by means (to be described later) on the filament 34 attached to the intraarterial anchor 32. Within a few hours after deployment, the anchor 32 will be coated with fibrin and thus attached firmly to the arterial wall, thereby eliminating the possibility of distal embolization. After approximately thirty days, only a small deposit of anchor material will remain. In fact, resorption of all components will have occurred after approximately sixty days.

The anchor member 32 is non-hemostatic and is sized to be hemodynamically insignificant in comparison to the size of the femoral artery. Thus, the resorbable anchor 30 has an insignificant hemodynamic effect on blood flow.

As will be appreciated by the description to follow deployment of the closure device 22 by the instrument 20 is easy, quick and reliable. Anchoring is repeatable, safe, and effective to deploy the collagen plug. Hemostasis occurs almost instantaneously, e.g., in 15 seconds or less, when the closure device is deployed properly.

Figure 2:
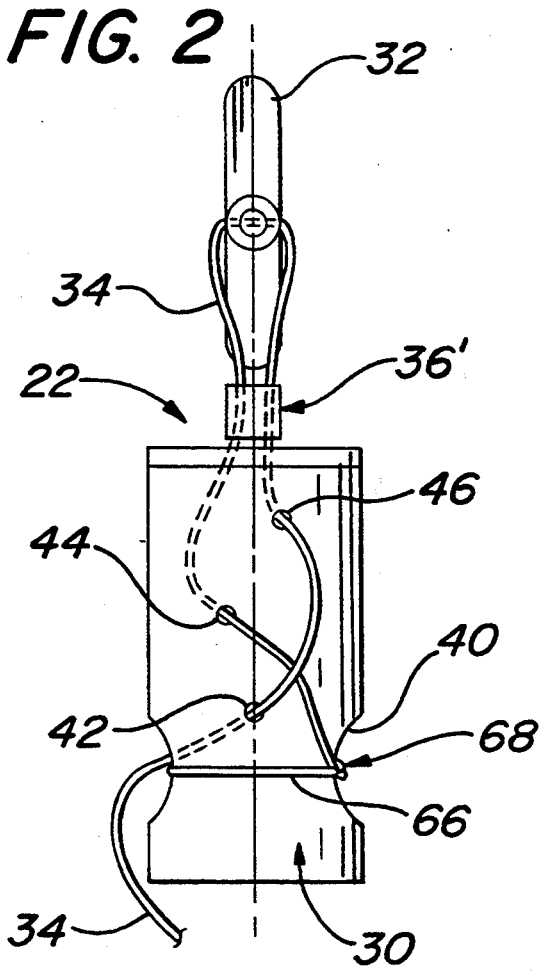
FIG. 2 is an enlarged, top plan view of the closure device shown in FIG. 1, with the sealing component shown in an uncompressed state.
Figure 3:
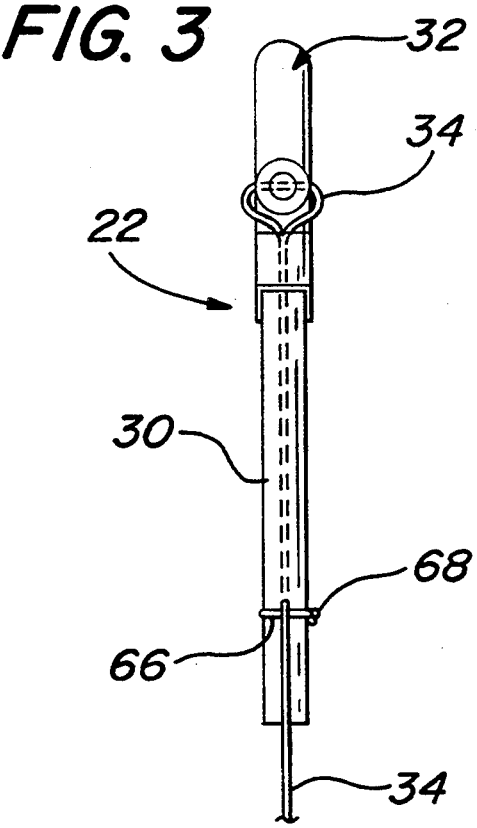
FIG. 3 is a top plan view, like that of FIG. 2, but showing the sealing component in its compressed state ready for deployment by the instrument of FIG. 1.

Referring now to FIGS. 2–5 the details of the closure device 22 will now be described. As can be seen in FIG. 2 the sealing member or plug 30 comprises a cylindrical member formed of a compressible, resorbable, collagen foam, such as that sold by Colla-Tec, Inc. of Plainsboro, N.J. The plug 30 is arranged to be compressed from the large diameter configuration shown in FIG. 2 to the small diameter, elongated configuration shown in FIG. 3. In the configuration of FIG. 3 the diameter of the plug is very small, e.g., 1.32 mm, and therefor suitable for disposition within the instrument 20, as will be described later. The plug 30 includes an annular recess 40 extending about its outer periphery adjacent its proximal end. Three apertures 42, 44, and 46 extend through the plug. In particular, the aperture 42 is located close to the recess 40 and diametrically through the centerline of the plug. The aperture 46 is located close to the distal end of the plug and extends transversely through the plug on one side of the center-line. The aperture 44 is located between apertures 42 and 44 and extends transversely through the plug on the other side of the centerline. These apertures serve as passageways through which the filament 34 extends to connect the anchor member 32 to the plug member 30 and are spaced apart to preclude tearing of the plug.

The manner of connection of the plug member to the anchor member will be described later. Suffice it for now to state that the filament 34 of the closure device 22 serves to couple the plug component to the anchor component in an arrangement to effect the movement of the plug component toward the anchor component, once the anchor component is in its desired position in the artery at the puncture or incision. In particular the coupling of the plug component to the anchor component simulates a pulley to achieve a desired mechanical advantage.

Figure 4:
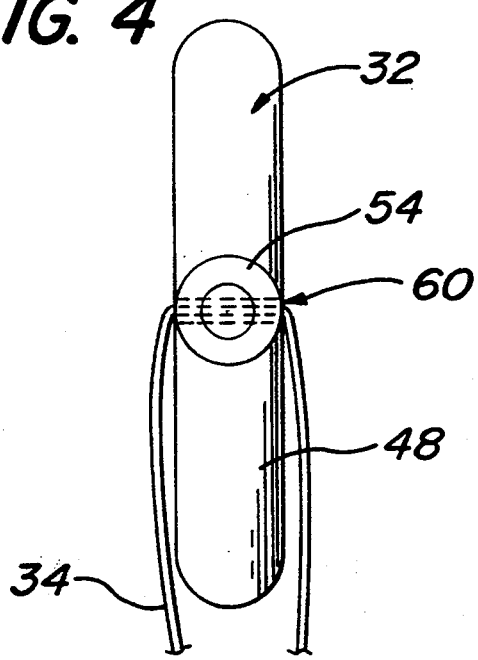
FIG. 4 is an enlarged, top plan view of the anchor component of the closure device.
Figure 5:
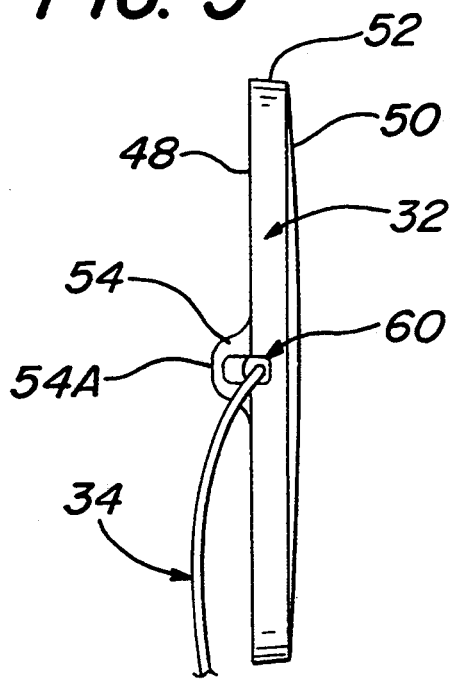
FIG. 5 is an enlarged, side elevation view of the anchor component of closure device.

As can be seen in FIGS. 4 and 5 the anchor member 32 basically comprises a thin, narrow, strip or bar of material, such as a resorbable lactide/glycolide polymer sold by Medisorb Technologies International L.P. under the trade designation MEDISORB. The strip is sufficiently rigid such that once it is in position within the artery (as will be described later) it is resistant to deformation to preclude it from bending to pass back through the puncture in the artery through which it was first introduced. The member 32 has a generally planar top surface 48, a radially contoured bottom surface 50 and a peripheral side surface 52. Each end of the member 32 is rounded. The side surface 52 of the anchor member 32 tapers inward slightly from its top surface 48 to its bottom surface 50 as shown in FIG. 5 to facilitate the removal of the plug from the mold for making it. A hemispherical dome-like projection 54 is located at the center of the top surface 48. The top surface of the projection 54 is slightly flatted at 54A (FIG. 5).

Figure 6:
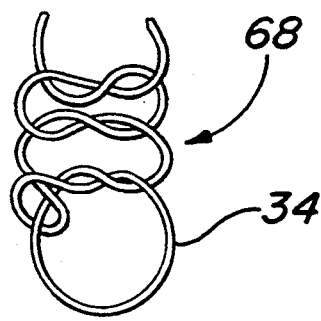
FIG. 6 is a greatly enlarged plan view showing the knot used to effect the securement of a filament component of the closure device to the sealing component thereof.

A cylindrical opening 60 extends transversely across the member 32 through the projection 54. In particular the filament 34 is threaded through the cylindrical opening 60 as shown clearly in FIG. 5 to connect the plug member 30 to the anchor member 32. In this regard the pulley-like connection between the anchor member and the plug member is effected by threading the filament 34 from a remote point in a chamber (to be described later) in the proximal portion of the deployment instrument through the transverse aperture 42, down the plug to the aperture 46, through that aperture to the opposite side of the plug and from there to the spacer member 36′ where it is threaded through the longitudinal opening 36′A in the spacer member 36′ and from there to the anchor member where it is threaded through the opening 60 as described earlier. From there the filament 34 extends through the opening 36′B in the spacer member 36′ and then back to the plug where it enters into aperture 44, passes through the aperture to the opposite side of the plug, where it terminates in a loop 66 extending around the annular recess 40. The loop is secured by a knot 68, whose details are shown in FIG. 6. In the alternate embodiment 36 of the spacer having the single central lumen 36A the filament 34 extends through that lumen going to the anchor member and returning from the anchor member.

Both embodiments 36 and 36′ of the spacer are formed of a resorbable material, such as the polymer MEDISORB as described previously. Each component can also include means to enable the component to be imaged radiographically to facilitate the placement of the closure at the desired situs within the patient's body or to monitor the resorption of the closure. One configuration of the spacer member 36 can contain a plug or powder of a conventional radiopaque material, which is preferably biocompatible and which is excretable, e.g., solid agents of sodium diatrizoate, iohexal, etc.

Referring now to FIGS. 1 and 15 the details of the deployment instrument 20 will now be described. As can be seen the instrument basically comprises a carrier 100 in the form of an elongated tube 102 formed of a somewhat flexible material, such as polyethylene, polyurethane, or TEFLON, so that the carrier may be freely passed through the introducer sheath into an operative position within the patient's artery, notwithstanding any curvature of the introducer sleeve which may exist. In accordance with a preferred embodiment of this invention the outside diameter of the tubular carrier 100 is 8 French. The distal end 102 of the tubular carrier 100 includes a rigid, e.g., stainless steel or polycarbonate, sleeve or bypass tube 104 mounted thereon, to enable the distal end 102 of the carrier 100 to be inserted through a conventional hemostasis valve 28A (FIGS. 12–14) forming a portion of the introducer sheath 28, through the sheath, and out the distal end thereof through the puncture tract 24A and the puncture or incision 24 into the artery 26. The distal end of the flexible tube 102 necks down into a generally hemicylindrical configuration (See FIG. 1) which includes a longitudinally extending slit (not shown) therein to enable it to be fit within the bypass tube 104 without buckling.

Figure 12:
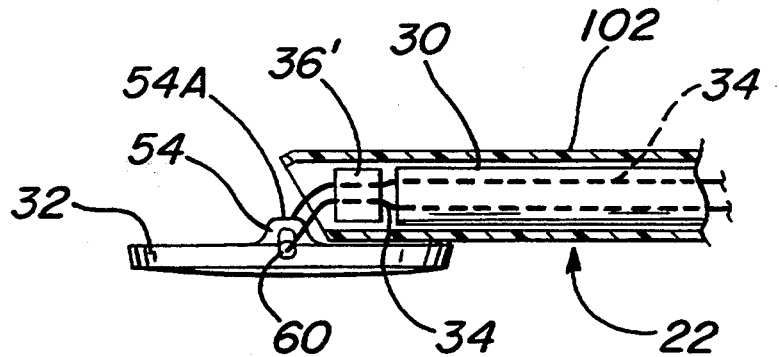
FIG. 12 is an enlarged, side elevation view partially in section, showing the distal portion of the deploying instrument containing the closure device of this invention.

As can be seen in FIGS. 1 and 12, the closure device 22 is located partially within the distal end of the tubular carrier 102. In particular the anchor member 32 is disposed outside the distal end of the carrier 102 longitudinally within the bypass tube 104 and laterally of the central longitudinal axis 106 of the carrier. The spacer member 36 is located within the tube 102 just behind (proximally) of the anchor member. The plug member 30 is located within the tube 102 just behind (proximally) of the spacer member 36. The bypass tube 104 includes a reference indicator or mark 108 in its periphery located diametrically opposite to the position of the anchor member. The mark 108 serves as a visual guide to help the user orient the instrument 20 to a proper yaw angle with respect to its central longitudinal axis for insertion within the introducer sheath 28 as will be described later.

As can be seen in FIGS. 1 and 15, the proximal end of the instrument 20 includes a housing assembly 170 comprising a cover or cap member 112 serving as a handle, a tensioner support frame 110 having a recess 148 for a supply of filament 34, and a tensioner assembly 126. The proximal end of the tubular carrier 102 is secured to the distal end of the housing assembly 170. In particular, the proximal end of the carrier 102 is flared at 100A and is located within a corresponding shaped opening 174 in a capture member 122. The member 122 is an integrally molded member comprising a pair of sections 122A and 122B secured together by a living hinge 122C. The section 122A and 122B are arranged to be snap fit together as shown in FIG. 1. As can be seen section 122A includes the heretofore identified opening 176. The proximal end of the opening 176 is flared to receive the outwardly flared end 100A of the carrier tube 102. The section 122B includes a conical central portion 178 which is configured to fit closely within the flared end 100A of the carrier tube when the section 122B is snap fit to section 122A. A central passageway 180 is located within the conical portion 178 and communicates with the interior of the carrier tube 102 to enable the filament 34 to pass therethrough from the tension assembly 126.

As will be appreciated by those skilled in the art, the use of the capture member 122 facilitates the assembly of the deployment instrument by enabling the carrier tube to be quickly and easily connected to the housing/handle 170 without the need for any adhesive.

The capture member 122 is mounted within the cover 112 by the frame member 110. This member is an integral unit, also molded of a suitable plastic, and serves to mount the tensioner assembly and a supply of the filament within the cover. The cover is also molded of a suitable plastic material. The cover or cap member 112 is a hollow member which is snapped onto the frame 110. The tensioner frame 110 has two prongs 140 which extend longitudinally on opposite sides of the housing and are directed distally. These prongs will be described later. Suffice it for now to state that each prong has a widened portion 146 which is arranged to cooperate with and engage a portion of the introducer to effect the proper placement of the deployment instrument 20 as will also be described later.

The tensioning assembly 126 is located within the cover 112 and basically comprises a ball 116 and a compression leaf spring 120. The leaf spring 120 is a generally U-shaped member whose open end is located towards the distal end of the frame 110. The spring is held in place via a pin 118 on the frame 110.

Figure 30:
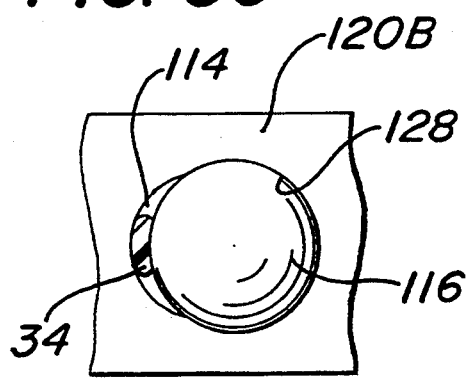
FIG. 30 is an enlarged plan view of a portion of the leaf spring shown in FIGS. 1, 28 and 29.

The ball 116 is located between the free ends of two legs or leaves 120A and 120B of the spring 120 in a conical recess 128 located in the free end of the leaf 120B. The proximally located portion of the filament 34 extends through the space between the ball 116 and the conical recess 128 in the spring 124. The amount of force applied to the ball is established by the spring force of the leaf spring 120. By appropriate selection of the spring, any desired preload can be applied to the filament. As can be seen clearly in FIG. 30, a small indentation or seat 114 extends in the conical recess 128 for approximately 120° of the periphery of the recess. This seat 114 provides a track for the filament 34 to pass therethrough. The seat's width is quite small, e.g., 0.003 inch (0.76 mm), but sufficiently large so that the filament 34 will not be crushed by the pressure applied to it from the spring loaded ball 116. In particular, the filament (suture) 34 cannot be crushed completely flat by the ball member 116 but will be deformed slightly to a predetermined finite thickness. In this regard, as will be appreciated by those skilled in the art, suture material and other polymers tend to deform when loaded by a force over an extended period of time. Such deformation can reduce the strength characteristics of the material. The seat 114 in the conical recess 128 limits the degree to which the ball 116 can deform the suture 34. Thus, as will be appreciated by those skilled in the art the tensioning assembly just described will tend to hold the filament in place with respect thereto until the force applied to the filament exceeds the preload force applied by the compression spring, whereupon the filament will be freed to slide through the instrument.

The carrier 100 also includes a tamping member 130. This member is an elongated rod-like member formed of any suitable material, e.g., polyethylene, and is disposed within the carrier tube 102 immediately proximally of the plug 32. The tamping member 130 includes a central passageway 132 extending down its length from its distal end 134 to its proximal end 136. The filament 34 portion extending from the anchor member 32 passes through the passageway 132 in the tamping member and from there through the proximal end of the carrier tube into the tensioner frame 110, through the tensioner assembly 126, and out through the seat 114 in the recess in the spring 124 into an annular storage space or recess 148 in the tensioner assembly 126. In particular, the space 148 is located within the frame 110 which supports the tensioner assembly. The suture filament is preferably stored as a coil inside the annular recess 148. However, if desired, the filament can be stored in any other compact and freely extendable manner, e.g., as a fan-fold configuration like a fire-hose. A disk or cap member 144 holds the filament in the recess 148. The annular recess is of a dimension such that a coil of the filament 34 ranging from approximately 1 inch (2.54 cm) to 5 inches (12.7 cm) in length and one suture diameter in height can be neatly stored therein.

Figure 10:
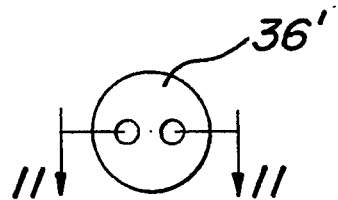
FIG. 10 is an enlarged, top plan view of an alternative preferred embodiment of a spacer component used in the closure of this invention.
Figure 11:
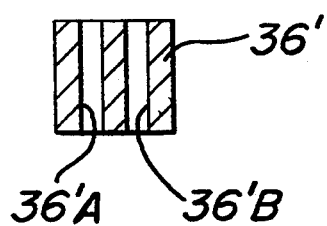
FIG. 11 is a sectional view taken along line 11—11 of FIG. 10.

A holding sleeve or tag 138, e.g., a stainless steel tube, is crimped onto the filament 34 so that it engages the proximal end of the tamping member 130 to hold that member in place. The tag 138 is arranged to cooperate with a torsion spring 142 (FIGS. 10 and 11) to apply tension onto the filament 34 after the closure 22 is in place to enable the instrument 20 to be removed and the filament 34 severed (as will be described later).

Figure 16:
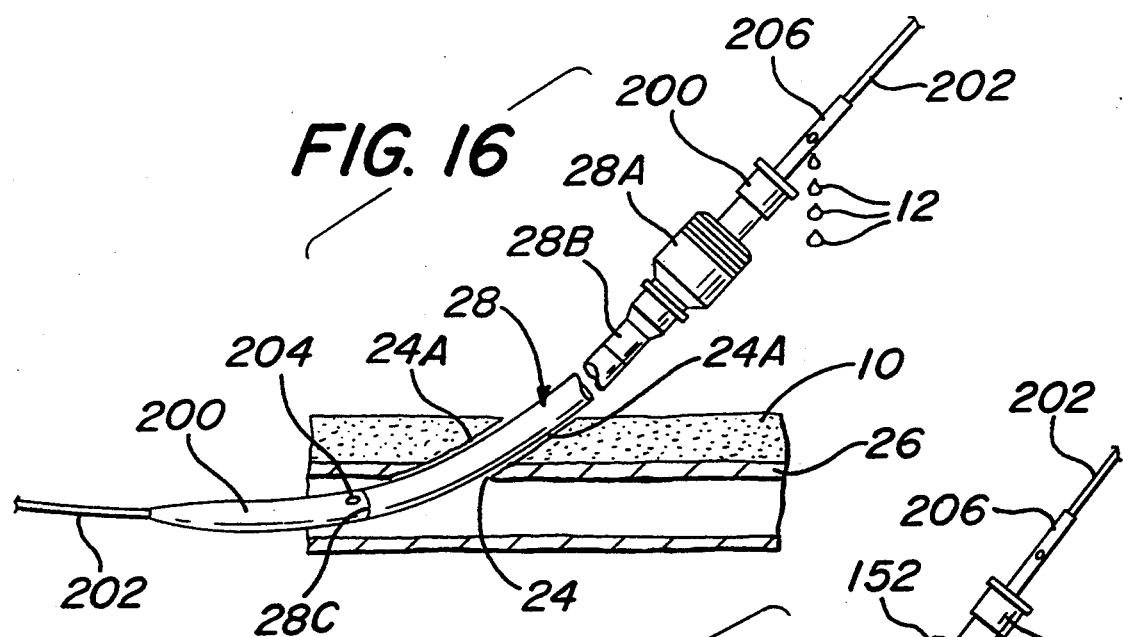
FIG. 16 is an illustration showing a preliminary step in the positioning of a conventional introducer sheath through a percutaneous puncture in an artery using the position indicating device shown in FIG. 7.
Figure 17:
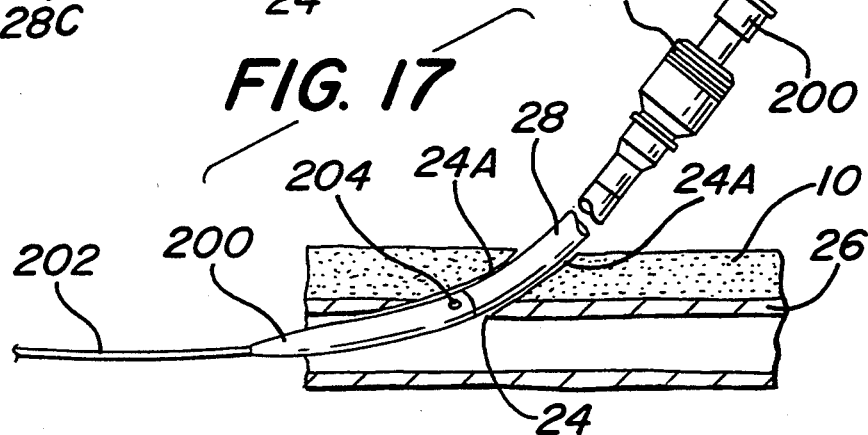
FIG. 17 is an illustration similar to that of FIG. 16 showing desired position of the introducer sheath within the artery as established by the use of the position indicating device shown in FIG. 7.

As mentioned earlier the instrument 20 is arranged to be inserted into a conventional introducer sheath 28 to effect the deployment of the closure device 20. Before describing that operation a brief description of the introducer sheath and its method of location with respect to the percutaneous puncture is in order. As can be seen in FIGS. 16–17 the sheath 28 includes a body portion or hub 28A in which a conventional hemostasis valve is located and a tubular portion 28B extending from the body. The tubular portion 28B terminates in an open distal or free end 28C.

Figure 7:
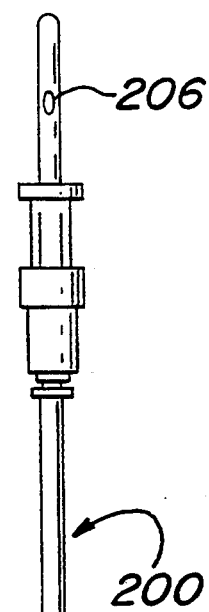
FIG. 7 is a top, plan view of an embodiment of a introducer sheath position indicating device forming a portion of the system of this invention.

Before the instrument can be inserted into the introducer sheath 28, the sheath itself must be properly located within the artery. This action is accomplished via a positioning device 200. That device is shown in FIG. 7. As can be seen the device 200 basically comprises a conventional dilator which has been modified to include two additional holes, namely, an entrance hole or port 204 and an exit hole or port 206. The device 200 is arranged to be fully inserted within the introducer sheath 28 like shown in FIG. 16. The holes 204 and 206 in the device 200 are connected by a hollow internal passageway or lumen (not shown) which extends along the length of the device. The location of the entrance port 204 is selected so that when the device 200 is fully with the introducer sheath, and the distal end of the sheath is within the interior of the artery, the entrance port 204 extends just beyond the distal end 28C of the introducer sheath to form a window into which blood may flow. The outlet port 206 is located on the proximal end of the surface 202 and is in fluid communication with the entrance port 204 via the internal lumen. Accordingly, blood may flow into the window 204 through the internal lumen of device 200 and out the exit port 206 as shown by the exemplary droplets 12 in FIG. 16.

In order to correctly position the introducer sheath the location of the artery wall must be established. This is accomplished by inserting the device 200 within the introducer sheath as just described and observing the flow of blood 12 from the outlet port 206 of the device 200. The blood will normally flow out of the outlet port by virtue of the pressure differential across the lumen wall. If, however, there is insufficient pressure to cause such a flow of blood, some means (not shown) can be used to create the desired differential pressure, e.g., suction can be used. In any event, once the flow of blood is observed the introducer sheath with the device therein is then retracted (moved proximally) until the blood flow through the outlet port just stops, a position shown in FIG. 17. This indicates that the distal end 28C of the introducer sheath has just left the artery lumen. The introducer sheath with the device therein is then reinserted approximately 10 mm into the puncture to ensure that the distal end of introducer sheath is at the desired position within the artery. Blood flow should be reestablished through the outlet port at this time. From this point the introducer sheath must be kept fixed, i.e., it must not move axially relative to the patient. To achieve that end the user of the system should provide a continuous grasp on the introducer sheath, with the patient's groin as a position reference. The position indicating device 200 is then removed from the introducer sheath to ready the introducer sheath for receipt of the deployment instrument 20 carrying the closure device 22 as will be described later.

Figure 18:
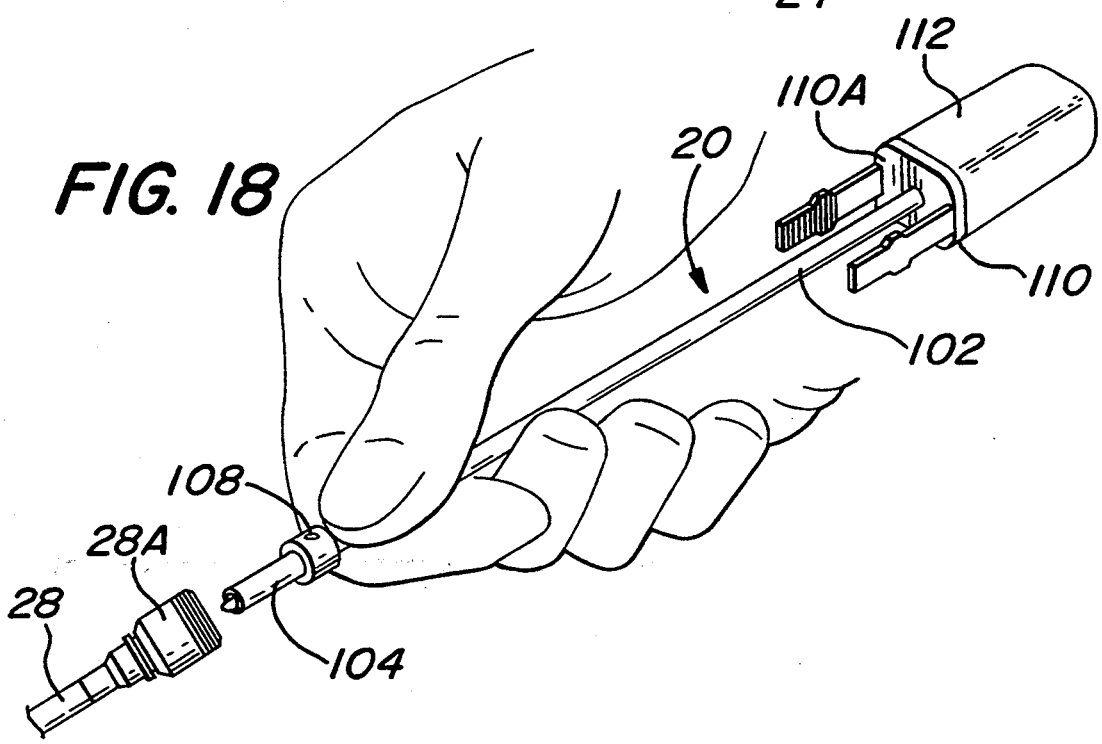
FIG. 18 is an illustration showing the introduction of the deployment instrument into the properly located introducer sheath.

The deployment of the closure will now be described with reference to FIGS. 18–26 and is as follows: The reference mark 108 on the bypass tube 104 is identified by the user and the bypass tube grasped by the user and oriented so that the mark 108 faces up (away from the patient) as shown in FIG. 18. This ensures that the anchor member 32 is located towards the patient.

The bypass tube 104 is then inserted into the sheath 28 through the hemostasis valve 28A. The rigid nature of the bypass tube facilitates the passage of the flexible carrier tube 102 through the hemostasis valve and protects the closure 22 from damage and from potential contamination from non-sterile materials. The instrument 20 is then pushed fully down the introducer sheath so that a stop surface 110A (FIG. 18) on the front (distal end) of the tensioner frame 110 (FIGS. 19 and 20) engages the hub 28A of the introducer sheath which houses the hemostasis valve. At this time the distal end of the carrier tube 102 will be in the position shown in FIG. 20 and the anchor member 32 will be located in the artery 26 beyond the distal end 28C of the introducer sheath 28. The bypass tube 104 remains within the hemostasis valve 28A of the introducer.

As can be seen in FIG. 1 and 15, each of the thin rectangular extension prongs 140 includes an intermediate widened section 146 located approximately halfway along the length thereof. The extension prongs serve as a means for measuring the distance which the instrument should be removed from the introducer 28 while testing for deployment of the anchor member 32, as will be described hereinafter. The system 20 is then operated to determine if the anchor member 32 has been properly deployed. To that end the introducer sheath 28 is held by the user to prevent axial movement and the deployment instrument 20 is carefully withdrawn from it. This action causes the anchor member 32 to engage or "catch on" to the distal end 28C of the introducer. As the anchor member catches on the distal end of the introducer, resistance will be felt by the user. This resistance must be noted by the time the indicators (widened portion) 146 of the extension prongs pass the proximal edge of the hub 28A of the introducer as shown in FIG. 21. If so, then the anchor member will have caught on the distal end of the introducer at the location of its hemispherical projection 54 (the desired occurrence). If, however, no resistance is noted by the time that the widened portion 146 of the indicator prongs 140 pass (extends proximally of) the proximal end of the introducer hub, this will indicate that the anchor member 32 has re-entered the introducer sheath, and that the anchor member will not catch onto the artery as required. Thus, if no resistance is felt at this point, the deployment instrument 20 must be reinserted within the introducer sheath 28 and the foregoing procedure retried, this time by turning the instrument 20 about its central longitudinal axis by approximately ¼ turn to each side before it is again withdrawn.

If the resistance is felt before the indicator portions 146 on the extension prongs 140 reach the distal end of the introducer hub this will indicate that one of the curved ends of the anchor member 32 has caught on the free end 28C of the introducer sheath, an undesirable occurrence. Accordingly, the instrument 20 must be reinserted within the introducer sheath 28 and the foregoing procedure retried, this time by turning the instrument 20 about its longitudinal axis by approximately ¼ turns to each side before it is again withdrawn.

Once the anchor member has been properly deployed, as shown in FIG. 21, the collagen plug 30 and spacer 36' are deployed next. To that end a light force is applied perpendicularly to the middle of each extension prong, in effect pinching the flexible prongs together as shown in a side view of the instrument in FIG. 22. As the force is applied the extension prongs will flex slightly until they contact the cap or hub portion 28A of the introducer 28. As shown in FIGS. 1 and 15 the inner surface of the extension prongs contain a series of parallel ridges 150. These ridges engage a series of annular recesses 152 which encircle the outer diameter of the introducer hub 28A. The surface geometry of the inner surface of the extension prongs and of the outer surface of the introducer hub are defined such that when the extension prongs are pinched together onto the hub, the ridges on the prongs enter the recesses on the hub. By grasping the extension prongs in such a manner, the instrument 20 and the introducer sheath 28 can be moved together as a single unit. In particular, while maintaining light transverse pressure upon the extension prongs, the instrument is steadily withdrawn as a unit from the puncture whilst swinging the instrument toward the vertical as shown in FIGS. 23 and 24. This action causes the anchor 32 to engage or catch onto the inner surface of the artery 26 contiguous with the puncture 24.

The continued retraction of the introducer sheath and the deployment instrument causes the filament 34 to pull the collagen plug 30 and the spacer 36' out of the carrier tube 102 and into the puncture tract 24A as shown clearly in FIG. 23. As the introducer and instrument come out of the puncture tract, as shown in FIG. 24, continuous steady resistance will be felt as the tensioner assembly described heretofore controls the force on the filament 34 during the retraction procedure. Continued retraction of the introducer and the instrument brings the tamping member 130 out of the free end of the instrument. Moreover, the pulley arrangement of the filament 24 connecting the anchor member and the plug member ensures that during the retraction of the introducer and the instrument, the plug member 30 and spacer member 36' are moved so that the spacer member engages the dome portion 54 of the anchor member 32 which extends through the puncture 24, and with the plug member 30 seated on the dome portion 54 spaced from the artery wall. In fact, continued retraction causes the filament 34 to somewhat deform the plug 30, i.e., causing it to deform radially outward.

The existence of blood within the puncture tract 24A further contributes to the deformation of the plug member 30 since the collagen foam expands in the presence of blood. The retraction procedure continues to pull the introducer sleeve and deployment instrument up the filament until the tag 138 is exposed, as shown in FIG. 25. At this point the anchor member 32 and collagen plug member 30 have been deployed. At this time the collagen plug is tamped by the tamping member 130. In particular, the user quickly compacts the collagen of the plug by gently tensioning the filament by pulling on the introducer sheath and instrument in the proximal direction with one hand. The tamping member is then manually slid down the filament by the user's other hand so that it enters the puncture tract 24A and engages the proximal end of the plug member 30. A few gentle compactions are adequate to achieve the desired result, i.e., to assist the plug member 30 in spreading out and conforming to the tract, thereby assisting in holding the plug in place until hemostasis occurs (which happens very quickly, thereby locking the closure in place).

As can be clearly seen in FIG. 27 when the closure 22 is in place the spacer member 36' (or member 36—if that spacer is used in lieu of 36') holds the collagen plug 30 away from the puncture 28 in the artery wall. In particular, the spacer 36' rests on top of the dome portion 54 of the anchor where that portion extends through the puncture 28, and does not contact the exterior of the artery wall. The plug 30 rests on top of the spacer 36' and is thus within the tract 28A below the surface of the skin but spaced from the puncture. The action of the spacer ensures that no portion of the collagen plug 30 will enter the artery (where it could conceivably break off and flow distally).

It should be noted that during the tamping action care must be taken to maintain tension on the filament 34 at a load greater than that used on the tamping member 130 to ensure that the tamping action doesn't propel the spacer member 36 and plug member 30 into the interior of the artery.

After the tamping action is completed a torsion spring 142, which is shown in FIGS. 13 and 14, and whose details will be described hereinafter, is mounted on the filament 34 as shown in FIG. 26. This action is necessary to maintain appropriate tension on the filament while the instrument 20 is removed (the filament severed).

In FIGS. 13 and 14 the torsion spring 142 is shown. As can be seen therein the spring 142 is a leaf spring which includes a pair of legs 142A and 142B projecting outward from a central section 142C. A portion of the each leg contains several rectangular shaped slots where material is removed and remaining material is bent upward, i.e., to form respective louvers 96. The louvers can be of any variety of shapes. These protrusions from the spring surface make the spring easy to grasp and handle and also serve to reduce the weight of the spring. Each spring leg includes a slot 142D (FIG. 14) at its free end. One of the slots is arranged to receive the filament 34 therein and to engage the tag 138. The other of the slots is arranged to receive the filament 34 therein and to engage the proximal end of the tamping member 130. The legs 142A and 142B are biased by the intermediate section 142C so that when the spring is mounted on the filament as just described they will bias the tamping means towards the plug member 30 to hold it in place so that the filament can be severed (as is necessary to remove the instrument and the introducer from the closure device).

Thus, once the spring is in place the filament on the proximal side of the tag 138 is cut and the spring applies a light controlled pressure to the collagen plug and anchor. The ends of each leg of the spring are shaped in a manner such that it is unlikely that the spring will be inadvertently dislocated from the suture. The closure is left in this condition without being disturbed for approximately 30 minutes.

After that time the spring 142 is removed and the filament is then severed at the top of the tamping member 130. The tamping member 130 is then removed and the remaining portion of the filament is cut subcutaneously prior to the discharge of the patient. With the closure in final position as shown in FIG. 27 the anchor member 32 (the only portion within the artery) does not take up a substantial portion of the interior of the artery and thus does not block off or otherwise impede the flow of blood therethrough.

Since the components of the closure are all formed of resorbable materials the closure can be left in place within the body until it is absorbed. Preferably the spacer 36' (or 36) includes some resorbable radio-opaque means therein. This enables one to radiographically image the site of the closure to determine when the closure has been absorbed by the body, whereupon a new percutaneous incision or puncture can be made at that site, if desired.

As should be appreciated by those skilled in the art the two sections of the filament 34 between the anchor component 32 and the plug component 30 effectively form a "pulley" arrangement to increase the mechanical advantage of the force applied to the filament to move the plug and anchor components toward each other. Accordingly, the closure can be properly seated without the application of a high pulling force. The use of the biased ball located in between the leaf spring between which the filament passes during the placing of the closure ensures that irrespective of how hard the instrument and the introducer are withdrawn from the puncture during the deployment and seating of the closure, the amount of force applied to the filament 34, and hence to the closure device, will not exceed a predetermined maximum, e.g., one pound. This feature is of considerable importance to ensure that the anchor portion of the closure is not pulled through the opening (e.g., incision or puncture) once it is in place.

As should also be appreciated from the foregoing, the closure device, the instrument for deploying it, and their method of use enables the ready, effective and efficient sealing of a percutaneous puncture in an artery or other blood vessel, duct or lumen. Thus, it is expected that the hemostatic puncture closure device 20 will be a significant advancement in the fields of cardiology and radiology. The device may allow continuance of anticoagulation post-procedure, more aggressive use of thrombolytic agents and safer use of large bore catheters. It should also reduce discomfort and complication rates for patients; allow many in-patient procedures to be performed safely on an out-patient basis; decrease the time and cost of interventional procedures; and reduce exposure of hospital personnel to human blood.

Without further elaboration the foregoing will so fully illustrate our invention that others may, by applying current or future knowledge, adopt the same for use under various conditions of service.

What is claimed is:

1. A method of sealing a small percutaneous puncture in a blood vessel of a living being, the percutaneous puncture comprising an opening in the vessel and a tract contiguous therewith extending through tissue overlying the vessel, said method comprising providing a closure comprising anchoring means, sealing means, and spacer means, inserting said anchor means within the vessel so that a first portion of said anchor means is in engagement with the interior of the vessel contiguous with the opening and a second portion is located within said opening, introducing said sealing means and said spacer means within the tract so that said sealing means is located spaced from the vessel, with said spacer means interposed between said sealing means and said anchor means, moving said spacer-means to a position spaced from the vessel but engaging said second portion of said anchor means, whereupon said spacer means prevents said sealing means from gaining ingress into the vessel via the opening.

2. The method of claim 1 wherein said closure means additionally comprises filament means, and wherein said method comprises coupling said anchor means, said sealing means and said spacer means together by said filament means, with said spacer means being interposed between said anchor means and said sealing means.

3. The method of claim 2 additionally comprising the step of pulling on said filament means to move said spacer means to a position within the tract spaced from the vessel but engaging said anchor means through the opening in the vessel and to cause said sealing means to engage said spacer means, whereupon said spacer means prevents said sealing means from gaining ingress into the vessel via the opening.

4. The method of claim 3 additionally comprising automatically ensuring that when said filament means is pulled the force applied thereto does not exceed a predetermined maximum value.

5. The method of claim 1 additionally comprising providing said closure means with radio-opaque means so that its position may be determined radiographically.

6. The method of claim 1 additionally comprising providing an introducer sheath and a deployment instrument, said introducer sheath having a distal end and a proximal portion, said deployment instrument having a distal end and a proximal portion, said closure being located within said deployment instrument, inserting said introducer sheath through the tract and the puncture into the interior of the blood vessel, introducing said deployment instrument into said introducer sheath until the distal end of said instrument is located distally of the distal end of said sheath, and utilizing an indicator member to measure the distance which said instrument should be moved proximally with respect to said introducer sheath to test for proper deployment of said anchor member within the blood vessel.

7. The method of claim 6 comprising the steps of holding the introducer sheath to prevent axial movement thereof and moving said introducer instrument proximally with respect thereto, to cause said anchor member to engage on to the distal end of the introducer sheath, whereupon some resistance will be felt by the user by the time that said indicator member has reached a predetermined point with respect to said proximal portion of said introducer sheath.

8. The method of claim 7 additionally comprising the step of retracting said introducer sheath and said deployment instrument together once said resistance is felt by the user by the time that said indicator member has reached said predetermined point, whereupon the anchor member engages the interior of said blood vessel contiguous with the puncture.

9. The method of claim 8 additionally comprising the steps of retracting said introducer sheath and said deployment instrument after said anchor member has engaged said interior of the blood vessel, whereupon said spacer means and said sealing means are pulled out of said deployment instrument and into the tract.

10. The method of claim 8 additionally comprising the steps of retracting said introducer sheath and said deployment instrument after said anchor member has engaged the interior of the blood vessel, whereupon said spacer means and said sealing means are pulled out of said deployment instrument and into the tract.

11. The method of claim 7 wherein said indicator member comprises at least one elongated prong, said prong having engagement means thereon for cooperating with engagement means on said proximal portion of said introducer sheath to effect the simultaneous retraction of said introducer sheath and said deployment instrument.

12. The method of claim 11 wherein said indicator member comprises a pair of opposed prongs, said method additionally comprising squeezing said prongs together to cause the engagement means of said deployment instrument to releasably engage the engagement means of said introducer sheath, whereupon said introducer sheath and said deployment instrument can be retracted simultaneously.

13. A method of sealing a percutaneous puncture in a blood vessel of a living being by providing a system comprising carrier means, introducer means, and closure means, the puncture comprising a tract extending through tissue overlying the vessel, said closure means comprising anchoring means, spacer means, sealing means, and filament means, said filament means connecting said anchoring means to said sealing means with said spacer means interposed therebetween, said introducer means comprising a tubular member having a distal free end, said method comprising the steps of inserting said introducer means into the puncture tract and through the puncture, inserting said carrier means through said introducer means, expelling said anchoring means from said carrier means into the vessel, drawing said anchoring means into engagement with said distal free end of said introducer means, moving said introducer means and said carrier means together to draw said anchoring means into engagement with the interior tissue of the vessel contiguous with the puncture, and drawing on said filament means to pull said anchoring means and said sealing means relative to each other so that said spacer means engages a portion of said anchoring means through the puncture, while preventing said sealing means from gaining ingress into the puncture.

14. The method of claim 13 additionally comprising automatically ensuring that when said filament means is pulled the force applied thereto does not exceed a predetermined maximum value 15. The method of claim 14 additionally comprising introducing tamping means into the tract to tamp said sealing means therein.

16. A system comprising an instrument and a closure for use therewith for sealing a percutaneous puncture in the wall of a blood vessel, the blood vessel having a longitudinal axis, the puncture comprising a tract contiguous with the opening and extending at an angle to the longitudinal axis of the vessel through tissue overlying the vessel, said closure means comprising anchoring means, sealing means, spacer means, and filament means, said anchoring means comprising an elongated, substantially stiff, member orientable with respect to said sealing means, said sealing means being expandable, said filament means being coupled to said anchoring means, said spacer means, and said sealing means, said instrument being insertable into the puncture tract and through the opening in the wall of the vessel for expelling said anchoring member therefrom, said anchoring member being arranged to be brought by said instrument into engagement with the interior tissue of the vessel contiguous with the opening on the inside of the vessel wall and generally parallel to the longitudinal axis of the vessel, said sealing means being arranged to be located within the tract remote from and outside the vessel wall, whereupon said sealing means is expanded to seal the tract from the passage of fluid therethrough, said spacer means being located within the tract interposed between said sealing means and said anchoring member to prevent said sealing means from gaining ingress into the vessel via the opening, said spacer means being spaced from the vessel but engaging said anchoring member through the opening in the vessel wall.

17. The system of claim 16 wherein said spacer means comprises a disk-like member having at least one passageway therein through which said filament extends.

18. The system of claim 16 wherein said spacer means comprises a resorbable material.

19. The system of claim 18 wherein said spacer means comprises a radio-opaque material.

20. The system of claim 16 wherein said instrument comprises a tubular carrier means in which a portion of said closure is located, and wherein said system additionally comprises an introducer through which said instrument is inserted into said puncture, said introducer comprising a distal free end portion and a proximal portion at which hemostatic valve means is located, said carrier means being arranged to pass through said hemostatic valve means.

21. The system of claim 20 wherein said tubular carrier means is formed of a material to enable it to flex and has a distal end portion for holding said sealing means and said spacer therein, and wherein said system additionally comprises a bypass sleeve disposed on the distal end of said tubular carrier for holding said anchoring member therein, said bypass sleeve being arranged to pass into said hemostatic valve to enable said carrier means to pass therethrough.

22. The system of claim 20 wherein said system additionally comprises position indicating means to provide a visual indication when said distal free end of said introducer means is located within the interior of the vessel and adjacent the puncture.

23. The system of claim 16 additionally comprising tensioning means mounted to a portion of said instrument and coupled to said filament means for preventing a force in excess of a predetermined maximum value from being applied to said filament means during the positioning of said closure means to seal the puncture.

24. The system of claim 23 wherein said tensioning means comprises a ball, a ball seat, an a relieved recess in a portion of the periphery of said ball seat, and spring means to bias said ball against said seat, with said filament extending within said relieved recess between said ball and said seat.

25. The system of claim 24 wherein said instrument comprises a tubular carrier means in which said closure is located, and wherein said instrument comprises a recess in which a supply of said filament means is located, with a portion of said filament means extending through said tensioning means, and down said tubular carrier means to said closure means.

26. The system of claim 25 wherein said filament means comprises a resorbable suture.

27. The system of claim 23 wherein said filament means comprises a resorbable suture.

28. The system of claim 16 wherein said instrument comprises a housing portion arranged to be held in the hand of a user, and wherein said instrument comprises a tubular carrier means in which a portion of said closure is located, said tubular carrier means having a proximal end releasably secured by a snap-fitting coupling located within said housing portion.

29. The system of claim 28 additionally comprising tensioning means located within said housing portion for preventing a force in excess of a predetermined maximum value from being applied to said filament means during the positioning of said closure means to seal the puncture.

30. The system of claim 29 wherein said tensioning means comprises a ball, a ball seat, an a relieved recess in a portion of the periphery of said ball seat, and spring means to bias said ball against said seat, with said filament extending within said relieved recess between said ball and said seat.

31. The system of claim 30 wherein said instrument comprises a tubular carrier means in which said closure is located, and wherein said instrument comprises a recess in which a supply of said filament means is located, said recess being located within the housing means, a portion of said filament means extending through said tensioning means, and down the tubular carrier means to said closure means.

32. The system of claim 16 wherein said anchoring means comprises an elongated member having a lower surface, and an upper surface having a generally domed projection at an intermediate point therealong, said upper surface being arranged to engage the interior of the blood vessel contiguous with said puncture so that said domed projection extends through said puncture, whereupon said spacer member is seated on top of said domed projection.

33. The system of claim 32 wherein said domed projection includes an opening through which said filament means extends.

34. The system of claim 32 wherein said sealing means is formed of a resorbable hemostatic material and wherein said anchoring means is formed of a resorbable non-hemostatic material.

35. The system of claim 34 wherein said sealing means is formed of collagen.

36. The system of claim 35 wherein said collagen is compressed prior to introduction into the body of the being and is arranged to automatically expand in the presence of blood.

37. The system of claim 16 additionally comprising tamping means arranged to be slid along said filament means to tamp said sealing means into the tract to cause said sealing means to spread out therein.

38. The system of claim 37 wherein said tamping means is mounted on said filament and arranged to slide therealong.

39. The system of claim 38 wherein said filament means is arranged to be pulled to cause said tamping means to be ejected from said instrument.

40. The system of claim 16 wherein said sealing means is formed of collagen.

41. The system of claim 40 wherein said collagen is compressed prior to introduction into the body of the being and is arranged to automatically expand in the presence of blood.

42. The system of claim 16 wherein said sealing means is formed of a resorbable hemostatic material and wherein said anchoring means is formed of a resorbable non-hemostatic material.

43. A closure for sealing a percutaneous puncture in a blood vessel having a longitudinal axis, the puncture comprising an opening in the vessel and a tract contiguous therewith extending at an angle to the longitudinal axis of the vessel through tissue overlying the vessel, said closure comprising anchoring means, sealing means, spacer means and filament means, said anchoring means comprising an elongated, substantially stiff, member orientable with respect to said sealing means, said anchoring member, said sealing means and said spacer means being coupled together by said filament means, said anchoring member being orientable with respect to said sealing means and insertable within the vessel so that a first portion thereof extends generally parallel to the longitudinal axis of the vessel and is in engagement with the interior of the vessel contiguous with the opening and with a second portion of said anchor means extending into the opening, said sealing means and said spacer means being insertable within the tract so that said sealing means is located spaced from the vessel, with said spacer means being interposed between said sealing means and said second portion of said anchoring member, said filament means being engagable to move said spacer means to a position spaced from the vessel but with a portion of said spacer means engaging said second portion of said anchoring member, whereupon said spacer means prevents said sealing means from gaining ingress into the vessel via the opening.

44. The closure of claim 43 wherein said spacer means comprises a disk-like member having at least one passageway therein through which said filament extends.

45. The closure of claim 43 wherein said spacer means comprises a resorbable material.

46. The closure of claim 43 wherein said spacer means comprises a radio-opaque material.

47. The system of claim 43 wherein said sealing means is formed of a resorbable hemostatic material and wherein said anchoring means is formed of a resorbable non-hemostatic material.

48. The closure of claim 47 wherein said anchoring member has a lower surface and an upper surface having a generally domed projection at an intermediate point therealong, said upper surface being arranged to engage the interior of the blood vessel contiguous with the puncture so that said domed projection extends through the puncture, whereupon said spacer member is seated on top of said domed projection.

49. The closure of claim 48 wherein said domed projection includes an opening through which said filament means extends.

50. The closure of claim 47 wherein said filament is resorbable.

51. The closure of claim 43 wherein said anchoring member has a lower surface and an upper surface having a generally domed projection at an intermediate point therealong, said upper surface being arranged to engage the interior of the blood vessel contiguous with the puncture so that said domed projection extends through the puncture, whereupon said spacer member is seated on top of said domed projection.

52. The closure of claim 43 wherein said sealing means is formed of collagen.

53. The closure of claim 52 wherein said collagen is compressed prior to introduction into the body of said being and is arranged to automatically expand in the presence of blood.

54. A system for sealing a percutaneous incision or puncture in the wall of a blood vessel of a living being, the blood vessel having a longitudinal axis, said system comprising carrier means, introducer means, and closure means, the puncture comprising a tract extending at an angle to the longitudinal axis through tissue overlying the vessel, said closure means comprising anchoring means, spacer means, sealing means, and filament means, said anchoring means comprising an elongated, substantially stiff member orientable with respect to said sealing means, said filament means connecting said anchoring member to said sealing means with said spacer means interposed therebetween, said introducer means comprising a tubular member having a distal free end arranged to be inserted into the puncture tract and through the puncture in the wall, said carrier means being arranged to be inserted through said introducer means to expel said anchoring member therefrom and to draw said anchoring member into engagement with said distal free end of said introducer means, said introducer means and said carrier means being arranged to be moved together to orient said anchoring member generally parallel to the longitudinal axis of the vessel and to draw said anchoring member into engagement with the interior tissue of the vessel contiguous with the puncture, said filament means being arranged to pull said anchoring member and said spacer means and said sealing means relative to one other, whereupon said spacer means prevents said sealing means from engaging the exterior of the blood vessel contiguous with the puncture.

55. The system of claim 54 wherein said introducer means comprises hemostatic valve means through which said carrier means is arranged to pass.

56. The system of claim 54 wherein said system additionally comprises position indicating means to provide a visual indication when said distal free end of said introducer means is located within the interior of said vessel and adjacent said puncture.

57. The system of claim 54 wherein said system additionally comprises position indicating means to provide a visual indication when said anchor means is in engagement with the distal free end of said introducer means.

58. The system of claim 57 wherein said position indicating means comprises at least one elongated prong on said carrier means, said prong having engagement means thereon for cooperating with engagement means on said introducer means to effect the simultaneous retraction of said carrier means and said introducer means.

59. A closure for sealing a percutaneous puncture in a blood vessel having a longitudinal axis, the puncture comprising an opening in the vessel and a tract contiguous therewith extending at an angle to the longitudinal axis of the vessel through tissue overlying the vessel, said closure comprising anchoring means, sealing means, spacer means and filament means, said anchoring means comprising an elongated, substantially stiff member orientable with respect to said sealing means, said anchoring member and said sealing means being coupled together by said filament means, said anchoring member being insertable within the vessel so that it extends generally parallel to the longitudinal axis of the vessel, with a first portion of said anchoring member being in engagement with the interior of the vessel contiguous with the opening and with a second portion of said anchoring member extending into the opening, said sealing means and said spacer means being insertable within the tract so that said sealing means is located spaced from the vessel, with said spacer means being interposed between said sealing means and said second portion of said anchoring member and in engagement with said second portion of said anchoring member, whereupon said spacer means prevents said sealing means from gaining ingress into the vessel via the opening.

60. The closure of claim 59 wherein said spacer means comprises a separate component of said closure and is coupled via said filament means to said anchoring means and said sealing member.

* * * * *